(12) United States Patent
Moloney et al.

(10) Patent No.: US 11,975,142 B2
(45) Date of Patent: May 7, 2024

(54) CONTROL DEVICE FOR AN ELECTRONIC AEROSOL PROVISION SYSTEM

(71) Applicant: Nicoventures Trading Limited, London (GB)

(72) Inventors: Patrick Moloney, London (GB); Anton Korus, London (GB); Justin Han Yang Chan, London (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 15/733,661

(22) PCT Filed: Mar. 27, 2019

(86) PCT No.: PCT/GB2019/050867
§ 371 (c)(1),
(2) Date: Sep. 25, 2020

(87) PCT Pub. No.: WO2019/186148
PCT Pub. Date: Oct. 3, 2019

(65) Prior Publication Data
US 2021/0007413 A1 Jan. 14, 2021

(30) Foreign Application Priority Data
Mar. 29, 2018 (GB) .................... 1805168

(51) Int. Cl.
*A61M 15/06* (2006.01)
*A24F 40/50* (2020.01)
(Continued)

(52) U.S. Cl.
CPC ............ *A61M 15/06* (2013.01); *A24F 40/50* (2020.01); *A24F 40/53* (2020.01); *A24F 40/65* (2020.01); *A24F 40/20* (2020.01)

(58) Field of Classification Search
CPC .......... A24F 40/65; A24F 40/53; A24F 40/50; A24F 40/60; A24F 40/51
See application file for complete search history.

(56) References Cited

U.S. PATENT DOCUMENTS 5,144,962 A 9/1992 Counts et al.
11,701,479 B1 * 7/2023 Robinson ................ A24F 40/30
128/200.16
(Continued)

FOREIGN PATENT DOCUMENTS

AU 2019244384 B2 10/2021
CA 2827144 A1 3/2015
(Continued)

OTHER PUBLICATIONS

Decision of Refusal received for Japanese Patent Application No. 2020-550617, dated Nov. 29, 2022, 5 pages (2 pages of English Translation and 3 pages of Official Copy).
(Continued)

Primary Examiner — Truc T Nguyen
(74) Attorney, Agent, or Firm — BURR & FORMAN LLP

(57) ABSTRACT

A control device for an electronic aerosol provision system is provided. The control device is configured to receive a replaceable component to form an electronic aerosol provision system. The control device includes a communication interface for performing communications external to the electronic aerosol provision system; a memory configured to hold a set of stored identifiers; and a control system. The control system is configured to: receive control information from a remote server via the communication interface; update the set of stored identifiers based on the control information received from the remote server; receive an identifier from a replaceable component received by the control device; make a comparison of the received identifier
(Continued)

against the set of stored identifiers; and perform a control action for the electronic aerosol provision system dependent upon the result of said comparison.

20 Claims, 4 Drawing Sheets

(51) Int. Cl.
*A24F 40/53* (2020.01)
*A24F 40/65* (2020.01)
*A24F 40/20* (2020.01)

(56) References Cited

U.S. PATENT DOCUMENTS

| | | | |
|---|---|---|---|
| 2009/0043613 | A1 | 2/2009 | Jung et al. |
| 2009/0090363 | A1 | 4/2009 | Niland et al. |
| 2009/0294521 | A1 | 12/2009 | De |
| 2013/0042865 | A1 | 2/2013 | Monsees et al. |
| 2013/0284192 | A1 | 10/2013 | Peleg et al. |
| 2014/0096781 | A1 | 4/2014 | Sears et al. |
| 2014/0334804 | A1 | 11/2014 | Choi |
| 2015/0105701 | A1 | 4/2015 | Mayer et al. |
| 2015/0245662 | A1 | 9/2015 | Memari et al. |
| 2015/0258289 | A1 | 9/2015 | Henry et al. |
| 2016/0338407 | A1* | 11/2016 | Kerdemelidis ......... A24F 40/60 |
| 2016/0346489 | A1 | 12/2016 | Finke et al. |
| 2017/0000192 | A1 | 1/2017 | Li |
| 2017/0020191 | A1 | 1/2017 | Lamb et al. |
| 2017/0042214 | A1 | 2/2017 | Murison |
| 2017/0048927 | A1 | 2/2017 | Murison et al. |
| 2017/0231277 | A1 | 8/2017 | Mironov et al. |
| 2017/0258136 | A1 | 9/2017 | Hawes et al. |
| 2018/0020733 | A1 | 1/2018 | Jochnowitz |
| 2019/0000144 | A1* | 1/2019 | Bless ................. G06K 7/10366 |
| 2019/0387796 | A1* | 12/2019 | Cohen ..................... A24F 40/30 |
| 2020/0000143 | A1* | 1/2020 | Anderson ............... G06F 18/22 |
| 2020/0338282 | A1* | 10/2020 | Trzecieski .............. A24F 40/53 |
| 2021/0134095 | A1* | 5/2021 | Milt ......................... A24F 40/65 |
| 2021/0251044 | A1* | 8/2021 | Reevell .................... G01F 23/22 |
| 2021/0378312 | A1* | 12/2021 | Talbot ..................... A24F 40/60 |
| 2022/0061399 | A1* | 3/2022 | Ferrie ..................... H02J 7/0047 |
| 2022/0202079 | A1* | 6/2022 | McGuinness .......... H02J 50/80 |
| 2022/0225684 | A1* | 7/2022 | Pueschner ............. B65D 85/20 |
| 2023/0200454 | A1* | 6/2023 | Li .......................... A24F 40/10 |
| | | | 131/329 |

FOREIGN PATENT DOCUMENTS

| | | |
|---|---|---|
| CA | 2940693 A1 | 9/2015 |
| CN | 1356783 A | 7/2002 |
| CN | 102264251 A | 11/2011 |
| CN | 103997921 A | 8/2014 |
| CN | 104303524 A | 1/2015 |
| CN | 105792687 A | 7/2016 |
| CN | 106136330 A | 11/2016 |
| CN | 106170215 A | 11/2016 |
| CN | 106455717 A | 2/2017 |
| CN | 106666834 A | 5/2017 |
| CN | 106998818 A | 8/2017 |
| EP | 0691083 A1 | 1/1996 |
| EP | 2201850 A1 | 6/2010 |
| EP | 3216357 A1 | 9/2017 |
| GB | 2542270 A | 3/2017 |
| JP | 2005198538 A | 7/2005 |
| JP | 2012513750 A | 6/2012 |
| JP | 2017510270 A | 4/2017 |
| JP | 2017513465 A | 6/2017 |
| JP | 2017522876 A | 8/2017 |
| JP | 2017531337 A | 10/2017 |
| KR | 20170121162 A | 11/2017 |
| RU | 2085092 C1 | 7/1997 |
| RU | 2517125 C2 | 5/2014 |
| RU | 2645324 C2 | 2/2018 |
| RU | 2647805 C2 | 3/2018 |
| TW | 201735805 A | 10/2017 |
| WO | 2009112182 A1 | 9/2009 |
| WO | 2011160788 A1 | 12/2011 |
| WO | 2015073854 A2 | 5/2015 |
| WO | 2015082560 A1 | 6/2015 |
| WO | 2015107552 A1 | 7/2015 |
| WO | 2016019353 A1 | 2/2016 |
| WO | 2016091658 A1 | 6/2016 |
| WO | 2016135271 A1 | 9/2016 |
| WO | 2016187695 A1 | 12/2016 |
| WO | 2016199066 A1 | 12/2016 |
| WO | 2017011419 A1 | 1/2017 |
| WO | 2017019428 A1 | 2/2017 |
| WO | 2017029089 A1 | 2/2017 |
| WO | 2017055801 A1 | 4/2017 |
| WO | 2017205692 A1 | 11/2017 |
| WO | 2018020599 A1 | 2/2018 |
| WO | 2018020619 A1 | 2/2018 |

OTHER PUBLICATIONS

Decision to Grant a Patent received for Japanese Patent Application No. 2020-548975, dated May 24, 2022, 5 pages (2 pages of English Translation and 3 pages of Official Copy).
International Preliminary Report on Patentability received for PCT Patent Application No. PCT/GB2019/050866, dated Sep. 22, 2020, 13 Pages.
International Preliminary Report on Patentability received for PCT Patent Application No. PCT/GB2019/050867, dated Oct. 8, 2020, 8 Pages.
International Preliminary Report on Patentability received for PCT Patent Application No. PCT/GB2019/050868, dated Oct. 8, 2020, 9 Pages.
International Search Report and Written Opinion received for PCT Patent Application No. PCT/GB2019/050866, dated Sep. 17, 2019, 18 Pages.
International Search Report and Written Opinion received for PCT Patent Application No. PCT/GB2019/050867, dated Jun. 6, 2019, 11 Pages.
International Search Report and Written Opinion received for PCT Patent Application No. PCT/GB2019/050868, dated Jun. 6, 2019, 15 Pages.
Invitation to Pay Additional Fees received for PCT Patent Application No. PCT/GB2019/050866, dated Jul. 22, 2019, 11 Pages.
Notice of Reason for Rejection received for Japanese Application No. 2020-549008, dated Sep. 21, 2021, 15 pages (7 pages of English Translation and 8 pages of Official Copy).
Notice of Reasons for Refusal received for Japanese Patent Application No. 2020-550617, dated Nov. 16, 2021, 8 pages (4 pages of English Translation and 4 pages of Official Copy).
Office Action and Search Report received for Chinese Application No. 2019800216825, dated Dec. 23, 2022, 11 pages (8 pages of English Translation and 3 pages of Official Copy of Search Report). ).
Office Action and Search Report received for Chinese Patent Application No. 201980023364.2, dated Dec. 27, 2022, 15 pages (12 pages of English Translation and 3 pages of Official Copy).
Office Action received for Chinese Patent Application No. 2019800227891, dated Jan. 20, 2023, 19 pages (9 pages of Official Copy and 10 pages of English Translation).
Office Action received for Korean Patent Application No. 10-2020-7027669, dated Jan. 18, 2023, 11 pages (6 pages of English Translation and 5 pages of Official copy).
Office Action received for Korean Patent Application No. 10-2020-7027669, dated Jul. 7, 2022, 9 pages (5 pages of English Translation and 4 pages of Official Copy).
Office Action received for Korean Patent Application No. 1020207028089, dated Jan. 20, 2023, 13 pages (7 pages of English Translation and 6 pages of Official Copy).
Office Action received for Korean Patent Application No. 10-2020-7028191, dated Jan. 30, 2023, 12 pages (6 pages of English Translation and 6 pages of Official Copy).

(56) References Cited

OTHER PUBLICATIONS

Office Action received for Russian Patent Application No. 2020131877, dated Apr. 28, 2021, 10 pages. (3 pages of English Translation and 7 pages of Official Copy).
Search Report received for Great Britain Application No. 1805170.6, dated Sep. 20, 2018, 4 Pages.
Search Report received for Russian Patent Application No. 2020131746, dated Jun. 10, 2021, 2 pages (Official Copy Only).
Search Report received for Russian Patent Application No. 2020131821, dated Jun. 21, 2021, 2 pages (Official Copy Only).

* cited by examiner

CONTROL DEVICE FOR AN ELECTRONIC AEROSOL PROVISION SYSTEM

PRIORITY CLAIM

The present application is a National Phase entry of PCT Application No. PCT/GB2019/050867, filed Mar. 17, 2019, which claims priority from GB Patent Application No. 1805168.0, filed Mar. 29, 2018, each of which is hereby fully incorporated herein by reference.

FIELD

The present disclosure relates to an electronic aerosol provision system.

BACKGROUND

The invention relates to an electronic aerosol provision system, which may also be referred to (for example) as an e-cigarette, vaping device, electronic vapor provision system (or device), and other similar terms. Many e-cigarettes include a reservoir of liquid (often synthetic) which is vaporized for inhalation. The liquid is more generally referred to as an aerosol precursor material. The reservoir of liquid may be provided in a replaceable component, frequently called a cartridge or cartomizer, which can be attached to, and detached from, the remainder of the e-cigarette.

Other e-cigarettes, sometimes referred to as tobacco heated products (THPs), may include an aerosol precursor (consumable) material derived from tobacco (or potentially from other plants). This aerosol precursor material is heated to produce a vapor for inhalation. Heating the THP consumable does not involve burning the THP consumable, i.e. pyrolysis, as for a conventional cigarette. The THP aerosol precursor material is typically in non-liquid form, e.g. dried leaves, solid powder, reconstituted plant material, gel, etc. In many cases, the THP consumable may include an outer container (such as one or more paper layers) within which an aerosol precursor material is provided. The THP consumable may be used only once, i.e. for one smoking session, analogous to a single (conventional) cigarette. This is in contrast to e-cigarettes having a liquid consumable, for which a cartridge may last for multiple smoking sessions, sometimes for multiple days. The rapid turnover of THP consumable containers means there is considerable interest in making them as simple and cost-effective as possible.

More generally, many electronic aerosol provision systems include a reusable component, often containing a control system and a re-chargeable battery, for use with a replaceable (disposable) component, often containing an aerosol precursor material (whether solid or liquid) that is used as a precursor for generating a vapor or aerosol for inhalation. During the lifetime of such an electronic aerosol provision system, the reusable component (also referred to as a control unit) may be utilized in conjunction with a number of different replaceable components (also referred to as consumables or cartridges). For example, a user may replace the replaceable component if its aerosol precursor material has been exhausted, or if the user would prefer to use a different replaceable component, such as one having an aerosol precursor for providing another flavor. Accordingly, it is desirable to be able to maintain good compatibility between a control unit and different replaceable consumables or cartridges that might be attached to, or received by, the control unit.

SUMMARY

A control device for an electronic aerosol provision system is provided. The control device is configured to receive a replaceable component to form an electronic aerosol provision system. The control device includes a communication interface for performing communications external to the electronic aerosol provision system; a memory configured to hold a set of stored identifiers; and a control system. The control system is configured to: receive control information from a remote server via the communication interface; update the set of stored identifiers based on the control information received from the remote server; receive an identifier from a replaceable component received by the control device; make a comparison of the received identifier against the set of stored identifiers; and perform a control action for the electronic aerosol provision system dependent upon the result of said comparison.

A method is provided for operating a control device for an electronic aerosol provision system, in which the control device is configured to receive a replaceable component to form the electronic aerosol provision system. The method comprises storing a set of identifiers in the control device; receiving control information from a remote server via a communication interface of the control device; updating the set of stored identifiers based on the control information received from the remote server; receiving an identifier from a replaceable component received by the control device; comparing the received identifier against the set of stored identifiers; and performing a control action for the electronic aerosol provision system dependent on the result of said comparing.

A server is provided for communicating control information to control devices, each control device being configured to receive a replaceable component to form the electronic aerosol provision system. The server comprises storage for maintaining a list of identifiers for the replaceable components; a processing system configured to update the list of identifiers in the storage; and a communications interface for transmitting the list of identifiers and for transmitting the updates to the list of identifiers to the control devices.

It will be appreciated that features and aspects of the disclosure described above in relation to the first and other aspects of the disclosure are equally applicable to, and may be combined with, embodiments of the invention according to other aspects of the disclosure as appropriate, and not just in the specific combinations described above.

BRIEF DESCRIPTION OF THE DRAWINGS

Various implementations of the disclosure will now be described, by way of example only, with reference to the accompanying drawings, in which.

DETAILED DESCRIPTION

The present disclosure relates to an aerosol provision device, also referred to as an aerosol provision system, an e-cigarette, a vapor provision system and similar. In the following description, the terms "e-cigarette" and "electronic cigarette" are generally used interchangeably with (electronic) vapor provision system/device, unless otherwise clear from the context. Likewise, the terms "vapor" and "aerosol", and related terms such as "vaporize", "volatilize" and "aerosolize", are generally used interchangeably, unless otherwise clear from the context.

Aerosol provision systems often have a modular design including, for example, a reusable module (a control or device unit) and a replaceable (disposable) cartridge module containing a liquid aerosol precursor material. The replaceable cartridge typically comprises the aerosol precursor and a vaporizer, such as a heater (and hence is sometimes referred to as a cartomizer), while the reusable module typically comprises the power supply, for example a rechargeable battery, and control circuitry. In some systems, the aerosol precursor may be a liquid, such as a synthetic e-liquid, contained in a reservoir within the cartridge module, which is then vaporized by heating. In some systems, the aerosol precursor material may be in a non-liquid form, such as dried leaves, solid powder, or gel, which are derived, for example, from tobacco plants. Such an aerosol precursor material may then be heated to release vapor. Some systems, which may be referred to as hybrids, may make use of both an e-liquid and a non-liquid aerosol precursor material. For example, in such a system the e-liquid may be vaporized by heating, and the resulting vapor passed through the non-liquid aerosol precursor to generate additional vapor and/or capture flavor from the latter.

It will be appreciated the reusable and disposable modules may include further elements depending on functionality. For example, the control unit may comprise a user interface for receiving user input and displaying operating status characteristics, and/or the replaceable cartridge part may include a temperature sensor for use in helping to control temperature.

In operation, a cartridge is typically electrically and mechanically coupled (in a removable fashion) to a control unit using (for example) a screw thread, latching or bayonet fixing with appropriately engaging electrical contacts. When the vapor precursor in the cartridge is exhausted, or the user wishes to switch to a different cartridge (perhaps having a different vapor precursor or flavor), the cartridge may be removed (detached) from the control unit and a replacement cartridge attached in its place. Devices conforming to such a two-part modular configuration may be referred to as a two-part device, although the approach described herein can also be applied if appropriate to devices having more than two components or modules.

Figure 1:
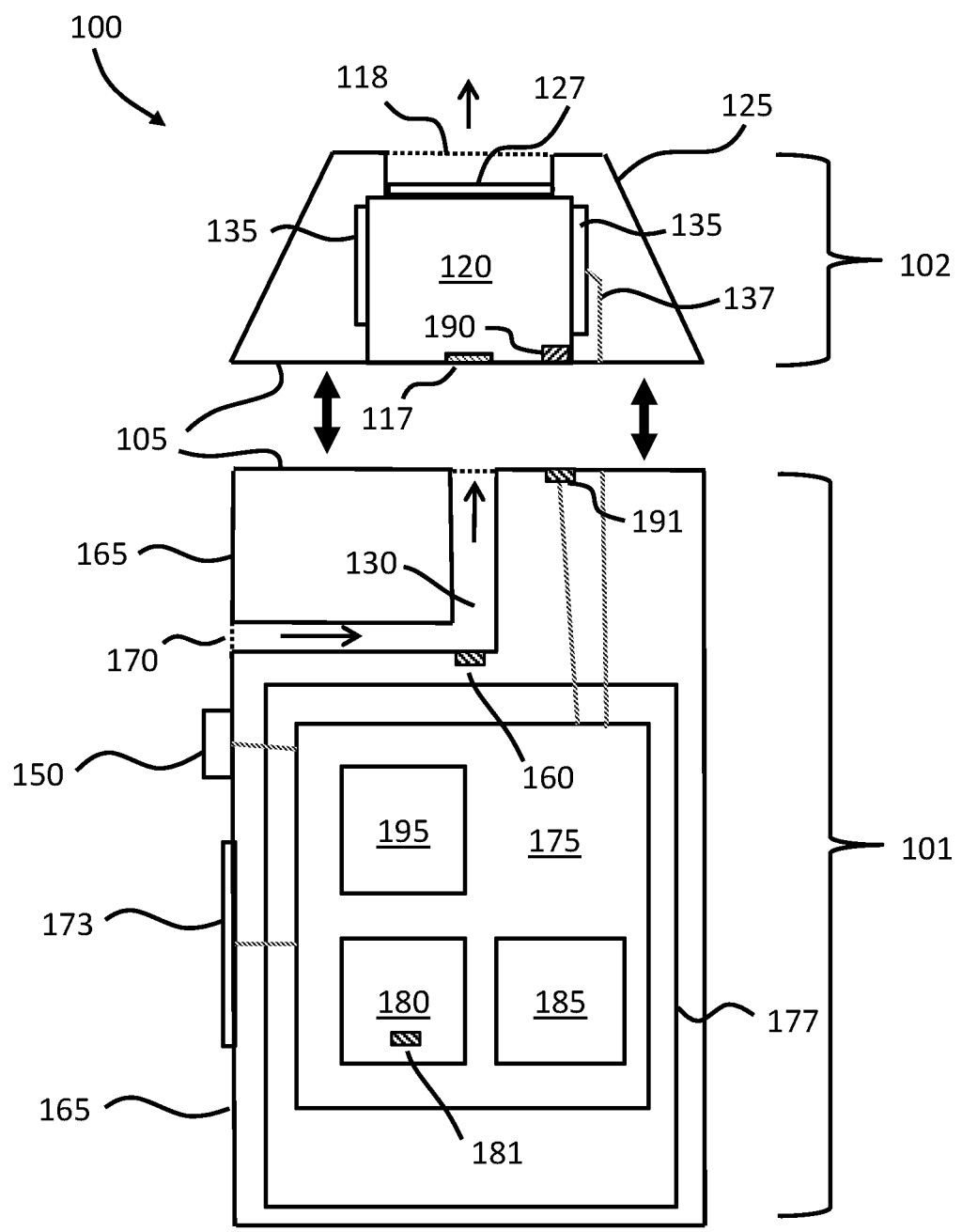
FIG. 1 is a schematic cross-section of an electronic aerosol provision device according to various implementations of the disclosure.

FIG. 1 is a schematic cross-sectional view through an example aerosol provision device 100. The aerosol provision device 100 comprises two main components or modules, namely a reusable/control unit 101 and a replaceable/disposable cartridge 102. In normal use the reusable part 101 and the cartridge 102 are releasably coupled together at an interface 105 (a connection interface) as shown by the two bi-directional arrows. The interface 105 generally provides a structural, electrical and air path connection between the two parts 101, 102 and may utilize a latch mechanism, bayonet fixing or any other form of mechanical coupling as appropriate. The interface 105 typically also provides an electrical coupling between the two parts, which may be wired using connectors, or may be wireless, for example, based on induction.

In FIG. 1, the cartridge 102 comprises a chamber or container 120 for holding an aerosol precursor material; in one example described herein, this material is a solid or non-liquid material such as dried leaves, solid powder, gel, etc. which provides an aerosol (for user inhalation) via the application of heat. In particular, the material container 120 is formed within an outer shell or housing 125. In the example, the outer shell 125 is further structured as a mouthpiece to provide an air outlet 118. In other examples the mouthpiece may be a separate component with the outer shell 125 configured to attach between the reusable part 101 and the mouthpiece.

The housing 125 and the mouthpiece may be provided as one integral component, formed directly as a single unit at manufacture, or may be formed from two parts which are then assembled together at manufacture in a substantially permanent fashion. For example, the housing 125 and mouthpiece may be fixed to each other along a join by friction welding, spin welding, ultrasonic welding, and so on (or by any other suitable technique). The cartridge housing 125 may be formed of plastic. It will be appreciated that the specific geometry of the housing 125, along with the materials, sizing, etc., may vary according to the particular design of a given implementation.

In some examples, when the cartridge 102 is exhausted or the user wishes to switch to a different cartridge, the cartridge 102 may be removed from the reusable part 101 and a new cartridge 102 attached to the reusable part 101 in its place. In the same or other examples, a user may be able to remove the solid material container 120 from the housing 125, for example, in order to provide a new solid material container 120 that includes fresh tobacco or other material. In this way the same cartridge may be reused if necessary. It will be appreciated that such a cartridge 102 will generally have a chamber or similar configured to receive the container 120.

The cartridge 102 has a heater 135 for heating the material contained in the material container 120. The heater 135 may be, for example, an electrically resistive heater, a ceramic heater, and so on. The heater 135 may form one or more walls or boundaries of the material container 120. The heater 135 is configured to provide heat to the material in material container 120 such that it is heated sufficiently to produce an aerosol for inhalation, but not to such a high temperature that the material in material container 120 combusts.

In use, the cartridge 102 is attached to reusable part 101 to allow the heater 135 to receive power by wires connected across interface 105 to the reusable part 101. Interface 105 is provided with electrical contacts or connectors, not shown in FIG. 1, to link wires 137 in the cartridge 102 with corresponding wires in the reusable part 101 (more generally, the wiring of FIG. 1 is shown only in schematic form, rather than indicating the detailed path and nature of such wiring). Some devices allow the heating power to be varied using a suitable control interface that alters the amount of power supplied to the heater 135 during activation. The adjustment in power level supplied from the reusable part to the heater 135 may be implemented using pulse width modulation or any other suitable control technique.

The device 100 may be activated by the user inhaling on mouthpiece 118, which triggers a puff detector or airflow sensor 160 to detect the airflow or change in pressure resulting from the inhalation. Other types of device may be activated additionally or alternatively by a user pressing a button 150 or similar on the outside of the device.

In response to a puff (inhalation) or button press being detected, the reusable part 101 provides electrical power to activate the heater 135 to create an aerosol. The aerosol thereby formed is drawn by user inhalation from the container 120, before exiting through mouthpiece 118 for inhalation by the user.

The solid material container 120 is linked to an airflow channel 130 by a first end wall 117 and (at the mouth end) by a second end wall 127. Each end wall 117, 127 is designed to retain the solid material in container 120 while allowing the passage of airflow along channel 130, through the container 120, and out through mouthpiece 118. This may be achieved for example by the end walls 117, 127 having suitably fine holes that retain the granules (or the like) of the solid material in container 120, but allow air to flow through the holes. The end walls 117, 127 of the material container 120 may be provided by separate retainers, for example in the form of disks which are inserted into each end of the housing 125 during manufacture. As an alternative, one or both of the end walls 117, 127 may be formed directly as part of the material container 120.

The reusable part 101 comprises a housing 165 with an opening that defines one or more air inlets 170 for the e-cigarette, a battery 177 for providing operating power to the device, control circuitry 175, a user input button 150, a visual display 173, and puff detector 160. In the configuration shown in FIG. 1, the battery 177 and the control circuitry 175 have a generally planar geometry, with the battery 177 underlying the control circuitry. The housing 165 may be formed, for example, from a plastics or metallic material and has a cross-section generally conforming to the shape and size of the cartridge part 102, so as to provide a smooth outer surface at the transition between the two parts at the interface 105. The battery 177 is rechargeable and may be recharged through a USB connector (not shown in FIG. 1) in the reusable part housing 165.

In the device 100 shown in FIG. 1, air pathway 130 starts at air inlet 170 of reusable part 101 and connects to the material container 120 through the interface 105. The puff detector (sensor) 160 is positioned within or adjacent to the airflow pathway 130 of the reusable part 101 to inform the control circuitry 175 when a user inhales on the device 100. The combination of the air inlet 170, airflow channel 130, material container 120 and mouthpiece 118 can be considered to form or represent the primary airflow path of the e-cigarette 100, whereby the airflow resulting from a user inhalation travels in the direction indicated by the single-headed arrows in FIG. 1, from air inlet 170 (upstream) to the mouthpiece 118 (downstream).

The user input button 150 may be implemented in any suitable fashion, e.g. as a mechanical button, a touch-sensitive button, etc., and allows various forms of input by the user. For example, the user might use the input button 150 to switch the device off and on (whereby puff detection to activate the heater is only available when the device is switched on). The user input button 150 may also be used to perform control settings, such as adjusting the power level. The display 173 provides a user with a visual indication of various characteristics associated with the electronic cigarette, for example the current power level setting, remaining battery power, on/off status and so forth. The display may be implemented in various ways, for example, using one or more light emitting diodes (LEDS) (potentially multi-colored) and/or as a small liquid crystal display (LCD) screen. Some e-cigarettes may also provide other forms of information to a user, for example using audio signaling and/or haptic feedback.

The control circuitry (alternatively controller or control unit) 175 may be provided by a printed circuit board (PCB) and/or other electronics or circuitry for generally controlling the aerosol provision device. The control circuitry 175 includes a processor 185 or microcontroller (or similar), which is programmed or otherwise configured to control the operations of the aerosol provision device 100, a non-volatile memory 180 for storing programming and/or configuration settings, and a communications interface 195 for communicating with systems and devices external to the device 100. The memory may include a set of stored identifiers 181 and other associated information as described later in more detail.

In operation, the control circuitry 175 may be notified of a puff detection from puff detector 160 and/or a press of button 150, and be configured to respond to such notification to supply electrical power from the battery 177 to the heater/vaporizer 135 through wires 137 to generate vapor for user inhalation. The control circuitry 175 can also monitor additional states within the device, such as the battery power level, and provide a corresponding output via display 173.

In some implementations, the characteristics of the aerosol substrate material in container 120, such as the flavor or nicotine strength, may vary, for example, with different batches or origins for different cartridges. As such, it may be useful for the identity of the material within container 120 to be made available to the control circuitry 175, which may store in memory 180 actions (programming) associated with different types of cartridge. For example, the programming may enable the control circuitry 175 to provide appropriate control signals and power levels for appropriate operation of the heater 135 for the given type of material within container 120. By way of example, the (flavor) compositions used in different aerosol precursor materials may deliver flavor at different rates or at different operating temperatures and, in order to ensure a consistent or an appropriate flavor delivery, control signals may be provided to provide suitable operation of the heater 135. In some cases, the programming may allow the selection of an appropriate heating profile in response to the identification of container 120, thereby enabling the material within the container 120 to be heated in a desired manner to ensure a particular user experience (and to help prevent undesirable effects such as burning of the material).

Different variants or types of container 120 (e.g., different types of aerosol precursor material therein) may be offered by a single manufacturer or by multiple difference manufacturers. As a result, there may be a large selection of different containers 120 having a range of attributes, features and so on available for use in the electronic aerosol provision system 100. As described herein, each container may have an identifier component 190 which may be recognized or otherwise interpreted by an identifying component 191 of the connection interface 105, thereby allowing the control unit 101 to determine (for example) the type and/or variant of the container 120 of cartridge 101 (and the material within).

As an example, the identifier component 190 may be an optically distinguishable pattern (such as a barcode) and the identifying component 191 may be an optical reader (such as a barcode scanner). In some cases, the bar code or other identifier may be arranged in a longitudinal direction, such that the optical reader scans along the bar code as the cartridge 101 is received into the control unit 102. In other implementations, the identifier component 190 may comprise a suitable electrical memory, such as ROM, a gate array, etc. In such implementations, the identifying component 191 may be implemented with the processor 185 (for example) to access an identifier from the electrical memory when the cartridge is coupled to (engaged with) the control unit 102. In other implementations, the identifier component 190 may comprise an RFID tag or similar, which is then read by the identifying component 191 when the cartridge is received into (or possibly just brought near) the control unit 102. It will be appreciated that there are many other methods which could be used by the identifier component 190 and the identifying component 191 to pass an identifier from the cartridge to the control unit.

A set of identifiers 181 may be stored in the memory 180 of the control circuitry 175, the identifiers typically relating different variants of the container 120 or cartridge. The set may include any number of identifiers; e.g., one identifier, or two or more identifiers. In some examples, each variant (i.e., each variant of aerosol precursor material, and/or of each container 120) may be assigned a specific identifier. In other examples, several variants may be grouped together and assigned the same identifier, for example if they share similar characteristics. By way of example, if two different flavors compositions release flavor at the same rate and/or at the same operating temperature, they may be assigned the same identifier.

The memory 180 may also be used to store actions or programming associated with each identifier. Such programming may be to select a certain heating profile for a given variant of cartridge (for example). There may be a one-to-one relationship between an identifier stored in memory 180 and the various heating profiles, or different groups of identifiers may correspond to different heating profiles.

In some implementations, the control circuitry 175 may process the identifier 190 prior to enabling heater 135 operation. For example, the control circuitry 175 may not supply power to operate the heater if container 120 (and the material within) are not suitable for use with that heater— such as because the heater is not powerful enough to vaporize the material within container 120. Operation may also be prevented if the identifying component 191 does not recognize the identifier received from the cartridge 102— this might indicate, for example, that the cartridge is a counterfeit or unlicensed product, and hence may not be properly compatible with the control unit 101. Accordingly, the set of stored identifiers may be controlled, for example, to ensure that only suitably authorized containers 120 or cartridges 102 are used with the control unit 101.

Accordingly, the present approach utilizes control circuitry 175 which is configured to identify the material container 120 and/or the cartridge section 102 attached for use with control unit 101. One or more characteristics of the cartridge may be deduced from the identifier received from the cartridge, and this information is then used by the control unit during subsequent use of the electronic aerosol provision system.

The set of stored identifiers in the control unit memory 180 may be updated, for example, when a new variant (of the cartridge 102 or container 120) is introduced, e.g. aerosol precursor material. One or more new identifiers for the new cartridge can be added to the set of authorized identifiers held in memory 180. Similarly, identifiers held in memory 180 may be removed or rendered obsolete when a variant is no longer sold. Furthermore, other updates may be performed, such as to alter the association of a particular identifier held in memory 180 with a variant, or to modify the actions stored or associated with the set of stored identifiers. For example, when a new identifier is added to the set of stored identifiers, corresponding actions (such as a new heating profile) may also be added. Additionally, in some cases the actions associated with an identifier may be modified without changing the identifier or its association with a particular variant. This updating of the set of stored identifiers 181 and/or their corresponding actions is facilitated by the communications interface 195 of the control circuitry 175. In some examples, the communications interface 195 may be a transceiver operable to communicate wirelessly with systems and devices external to the aerosol provision device 100. In some cases, an external system or device may act as an intermediary to support indirect communication between the aerosol provision device 100 and one or more remote servers etc.

Figure 2:
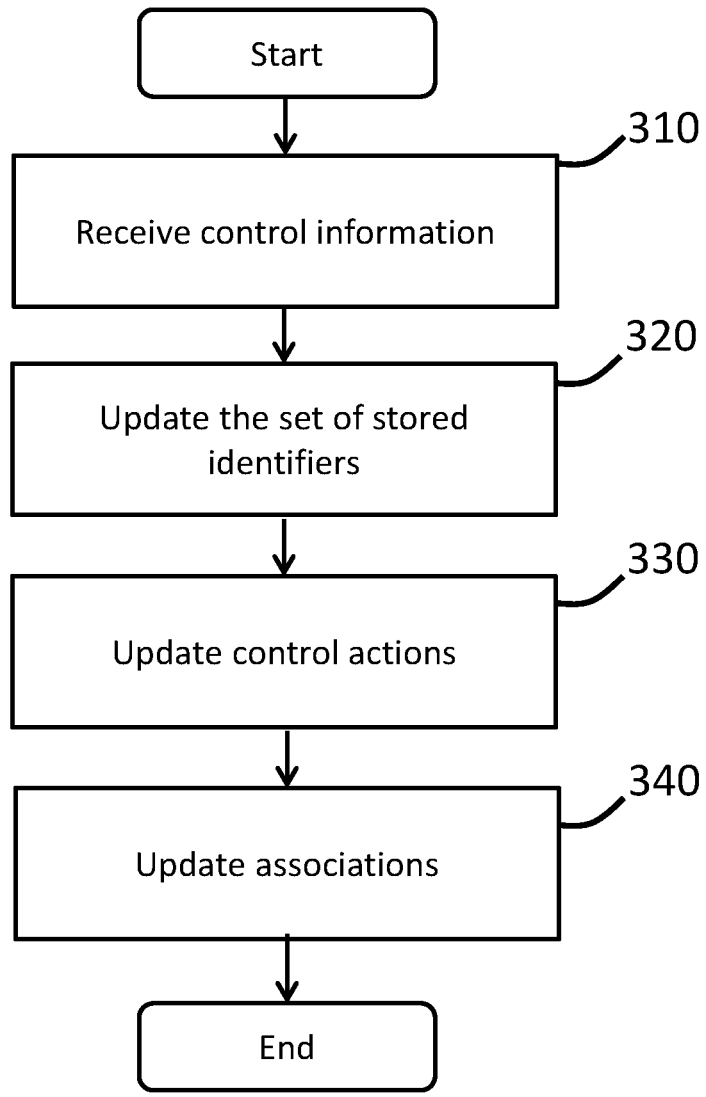
FIG. 2 is a schematic flow diagram of a method to be performed by a control unit according to various implementations of the disclosure.

FIG. 2 shows a flowchart of an example method of operating an electronic aerosol provision system 100 such as shown in FIG. 1 (or the control unit 101 thereof), the device having a memory 180 holding a set of stored identifiers 181. In 310, the control unit 101 receives control information from a remote server via the communication interface 195. According to the particular implementation, the communication interface 195 may support wired and/or wireless communications with an external device (i.e. external to the electronic aerosol provision system). The external device or system may either contain the control information (and so act itself as a remote server), or may facilitate access to a remote server storing the control information. For example, the external device or system might be a smartphone or a laptop or other local device that links over the Internet to the remove server. The received control information may comprise instructions to be performed (for example by the processor 185) and/or data, such as one or more identifiers. The instructions and the data may be saved into memory 180 (or any other appropriate storage device or component).

In 320, the control unit updates the set of stored identifiers based on the control information received from the remote server. Updates to the set of stored identifiers may include adding a new identifier to the set of stored identifiers, removing an identifier from the set of stored identifiers, and/or modifying an identifier of the set of stored identifiers, as appropriate.

In some cases, the control information may comprise a complete set of (updated) information relating to the stored identifiers. In this case, one option is for the control unit to overwrite all the control information previously stored in memory 180 with the newly received information. In other cases, the control unit may compare the newly received control information with the control information already held in memory, and only perform updates in respect of changed information (i.e. additions, deletions and/or modifications). In other cases, the control information may itself be formatted as a set of update actions (add this, delete, this and modify this).

In 330, the control unit updates control actions held in memory that relate (correspond) to various stored identifiers, based on the control information received from the remote server at operation 310. For example, each stored identifier may have its own respective control action, or a subset of stored identifiers may share a respective set of one or more control actions. As with the identifier updates, the format of the control action updates may vary according to the implementation—e.g. a complete overwrite of the previously stored control actions, or just selective updating.

In 340, the control unit updates associations between the identifiers in the set of stored identifiers and the control actions, based on the control information received from the remote server. For example, one of the stored identifiers may be associated with a newly provided (updated) control action, or an association may be updated to link a stored identifier with a different (but already stored) action. Furthermore, if a subset of stored identifiers is associated with a particular control action, the control information may update the identifiers within that subset, for example identifiers may be added or removed.

It will be appreciated that as for the identifier updates, the format of the control action updates and/or the association updates may vary according to the implementation—e.g. a complete overwrite of the previously stored control actions and/or associations may be performed, or just selective updating. In addition, some updates of received control information may not contain updates for stored identifiers, control actions and associations, but rather may contain updates for any one or two of these categories.

Figure 3:
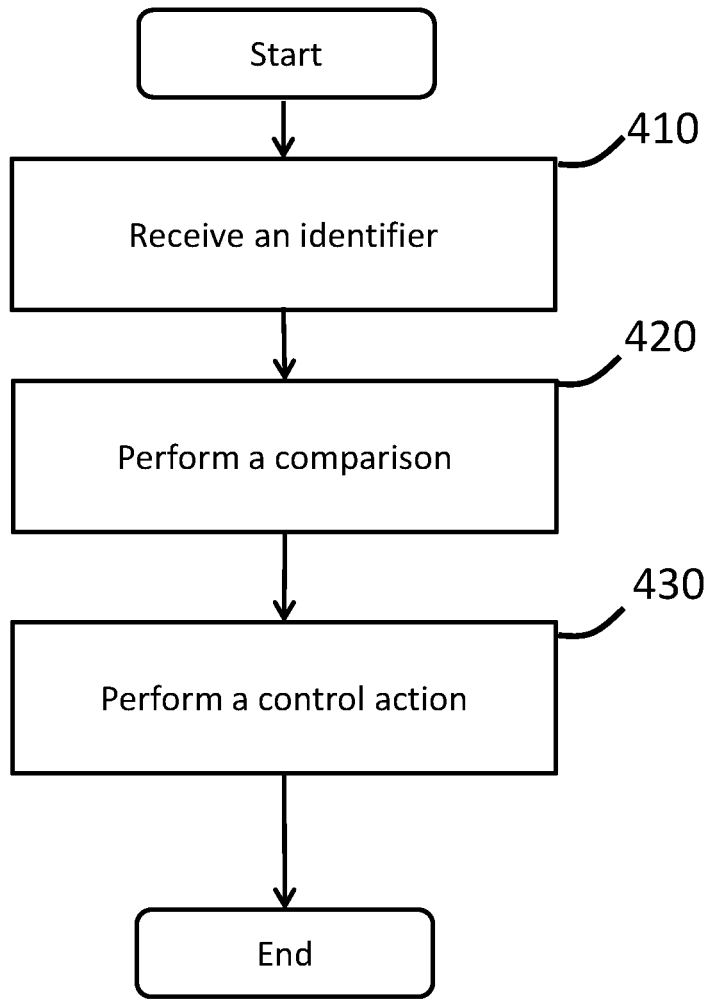
FIG. 3 is a schematic flow diagram of another method to be performed by a control unit according to various implementations of the disclosure.

FIG. 3 shows a flowchart of an example method of operating an electronic aerosol provision system 100 such as shown in FIG. 1 (or the control unit 101 thereof), whereby an identifier received from a cartridge is compared with a set of stored identifiers in memory 180. Note that the method of FIG. 3 may occur independently of, in parallel with, or subsequently to the method of FIG. 2.

In 410, the control unit 101 receives an identifier from a cartridge 102 or other consumable (disposable) component which is typically being engaged with (received into) the control unit 101 to form an electronic aerosol provision system. In some implementations, the identifier may be received over (or by) a connection interface 105 which is provided between the cartridge 102 and the control unit 101.

In 420, the control unit 101 performs a comparison of the received identifier against the set of stored identifiers held in memory. The control unit, for example, the processor 185 of the control unit, is configured to compare the received identifier with each identifier of the set of stored identifiers to determine whether the received identifier matches one of the stored identifiers. Finding a match may indicate, for example, that the cartridge can be considered genuine, and hence properly compatible with the control unit 101.

In 430, the control unit 101 performs some control action which is dependent upon the result of the comparison of 420. In some cases, the control action may be dependent upon whether the comparison finds any match for the received identifier in the set of stored identifiers—which may confirm that the cartridge 102 is genuine, as suggested above. In other cases, the control action may be dependent upon which particular identifier in the set of stored identifiers is matched by the received identifier. For example, matching different stored identifiers may correspond to applying different heating profiles to operation of the vaporizer. In some cases, there may be multiple control actions dependent upon the result of matching an identifier.

Furthermore, there may be a default control action (or actions) if no match is found between the received identifier and the set of stored identifiers. For example, the default control action may include disabling (or not enabling) the heater by preventing the supply of power to the heater. Alternatively, the default control action may enable operation of the heater, but typically in a more conservative manner than when the identifier is matched (e.g. for safety reasons). For example, it may be desirable to reduce the amount of heating to avoid potential disassociation of certain THP or e-liquid components that might possibly be present in a received replaceable component. However, this reduced amount of heating may also produce less vapor.

In contrast, a higher level of heating might be employed with a matched identifier if this higher level is known to be compatible with the THP or e-liquid components present in the identified replaceable component. In this context, having a matched identifier allows control actions to be optimized to the properties of the identified replaceable component, for example in terms of amount of heating and vapor production. In contrast, not having a matched identifier may lead to the use of default control actions and/or setting which might adopt a lowest common denominator (generic) approach in order to help compatibility with an unidentified replaceable component. This in turn may lead to sub-optimal operation (compared with having a matched identified), but might still be more attractive for a user than preventing operation altogether.

Figure 4:
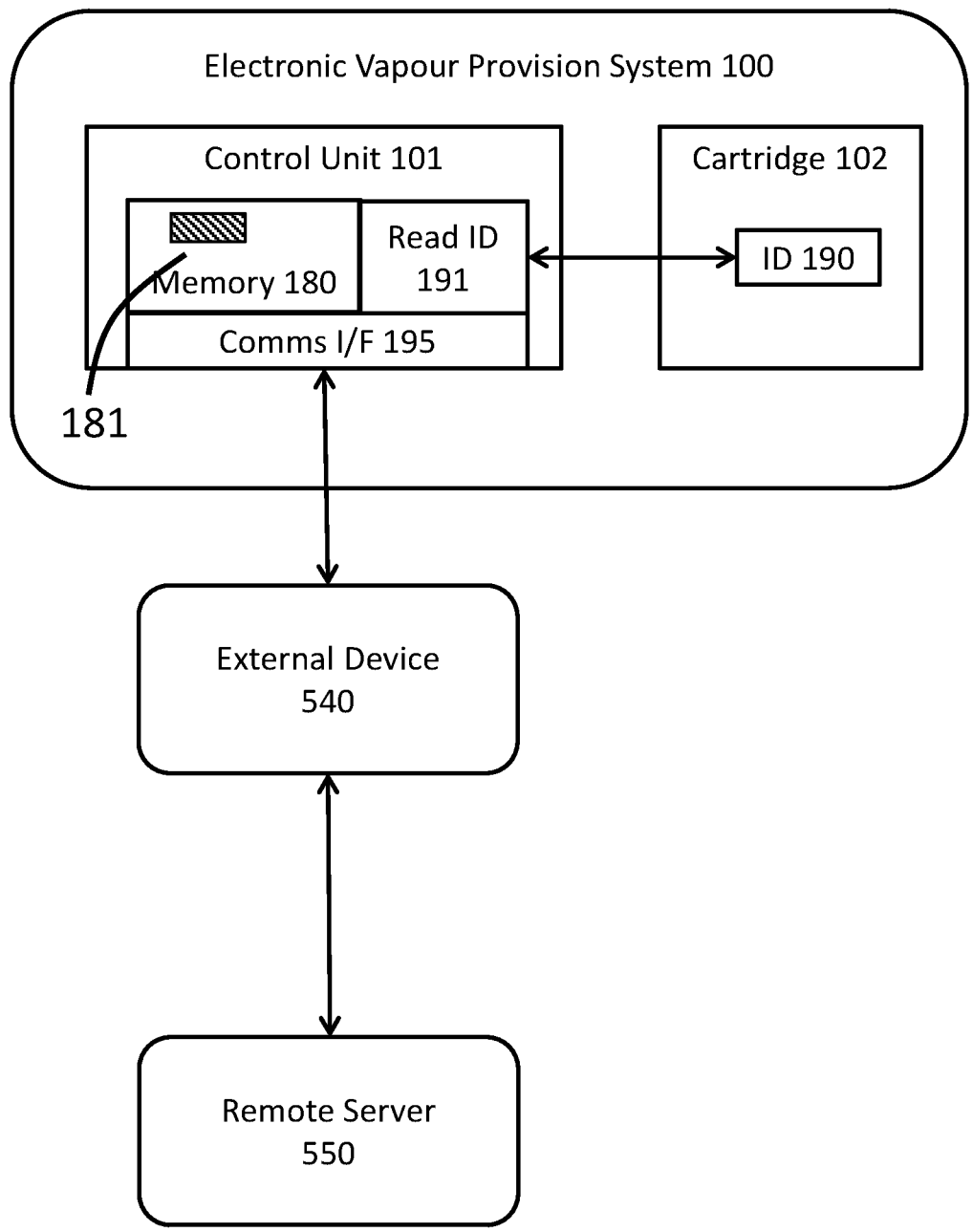
FIG. 4 is a schematic diagram showing communications between different systems and devices according to various implementations of the disclosure.

FIG. 4 is a schematic diagram showing communications between different systems and devices according to various implementations of the disclosure. In particular, FIG. 4 illustrates an electronic vapor provision system 100 (electronic aerosol provision system), such as shown in FIG. 1, comprising a re-usable component, such as control unit 101, and a replaceable component, such as cartridge 102. The cartridge 102 includes a consumable component (not shown), such as an e-liquid or a tobacco plant derivative (such as dried leaves). The consumable component acts as a vapor or aerosol precursor, and when heated generates a vapor/aerosol for inhalation by a user. The control unit 101 typically includes a rechargeable battery (not shown) for providing power to the heater used to generate the vapor/aerosol from the precursor material.

The cartridge 102 further includes an identifier (ID) component 190, which may be provided in various different ways as discussed above—for example as a bar code marking for optical reading, as an electronic memory, etc. The control unit 101 includes an ID reader 191 which is able to receive (e.g. read or access) the ID from the ID component 190, typically when the cartridge 102 is coupled to (engaged with or received into) the control unit 101, or perhaps when the cartridge is otherwise brought close to the control unit. It will be appreciated that the nature of the ID reader 191, and the specifics of how the ID is received from the cartridge 102, depend on (and correspond to) the implementation of the ID component 190. For example, if the ID component 190 comprises a bar code, then the ID reader 191 typically comprises some form of optical reader; if the ID component 190 comprises electronic memory, such as a ROM, then then ID reader 191 may be implemented as an electronic read facility, and may be incorporated (for example) into processor 185.

In addition to ID reader 191, the control unit 101 includes a communications interface 195 and a memory 180. The memory is used, inter alia, to hold a set of stored identifiers 181. The memory may also hold (or support access to) various control (operational) actions that are associated with the identifiers. For example, the control actions may comprise heating profiles (how long a heater should be operated and at what power levels), whether to allow operation of the device for vapor generation, display of messages to a user, and so on. The control unit 101 is configured to perform one or more control actions dependent upon the match (or otherwise) between the stored identifiers and the received identifier. Note that multiple stored identifiers may match to a given control action. For example, one heating profile may be suited for a first set of batch numbers for the cartridge 102, another heating profile may be suited for a second set of batch numbers for the cartridge.

The list of identifiers 181 is maintained by communications between the electronic vapor provision system 100 and a remote server 550. FIG. 4 shows an external device 540, such as a smartphone and app, mediating these communications (which typically occur over the Internet), however, in some cases the electronic vapor provision system 100 and the remote server 550 may be able to communicate directly with one another, so that external device 540 may be omitted. The communications interface 195 may be implemented in various ways, for example, using a USB link (which may also be used for recharging the battery in the control unit 101) or by using a wireless connection such as Bluetooth to the external device. In some devices, the communication interface 195 may support multiple forms of connectivity.

The control unit 101 may receive updates for the stored identifier listing 181 from the remote server 550 at various times, for example, the control unit may contact the remote server 550 when network connectivity is established (and optionally when such contact has not been performed for a given time period). The control unit 101 may also contact the remote server if the control unit 101 receives an identifier from the cartridge 102 that it does not recognize, i.e. that does not match anything in the list of stored identifiers 181. The remote server may then be able to provide an up-to-date match for this identifier (if available).

In some systems, the control unit may be configured to always request information from the remote server 550 for an identifier which is newly received from a cartridge 102. In this case, the control unit may not include memory 180, which can reduce costs. On the other hand, having the stored set of identifiers 181 in memory 180 allows the matching of the received identifier to be performed more quickly, without any communication delays (and without requiring any network connectivity).

As described herein, a control device for an electronic aerosol provision system is provided. The control device is configured to receive a replaceable component to form an electronic aerosol provision system. The control device includes a communication interface for performing communications external to the electronic aerosol provision system; a memory configured to hold a set of stored identifiers; and a control system. The control system is configured to: receive control information from a remote server via the communication interface; update the set of stored identifiers based on the control information received from the remote server; receive an identifier from a replaceable component coupled to the control device; make a comparison of the received identifier against the set of stored identifiers; and perform a control action for the electronic aerosol provision system dependent upon the result of said comparison.

In some implementations the replaceable component contains a consumable material, such as an aerosol precursor material. The control action may be targeted at the particular consumable (aerosol precursor) material contained in the replaceable component, for example, the control action may specify how best to generate an aerosol from the aerosol precursor material. In other implementations, the replaceable component might not contain an aerosol precursor material. For example, the control unit might initially be supplied with a first, non-refillable (by the user), replaceable component. This initial replaceable component may then be removed and replaced by a second replaceable component, which is empty of a consumable material when received into the control unit, but may be subsequently be (re)filled by the user with an aerosol precursor material for use as an electronic aerosol provision system.

In some implementations, the replaceable component may be an element which is attachable to the control unit and is intended to be replaced periodically. For example, it is known in some THP devices for a tubular sleeve to be inserted into a heating chamber of the control unit, with rod-like consumables then being inserted into the sleeve for heating. Each pack of 20 consumables may be provided with such a sleeve. For such an arrangement, it may be easier (and more cost-effective) to provide the identifier on each sleeve (as a replaceable component), rather than on every rod-like consumable.

The identifier received from the replaceable component may comprise (or consist of) information specific to the replaceable component, for example, one or more of a unique serial number, a model number, a date of manufacture, a use-by date, an authentication code, information about the consumable material in the replaceable component such as batch number, blend or flavor, one or more operating parameters to apply in the control device (control unit), such as a heating profile, information to provide to a consumer, such as a description of the consumable material in the replaceable component.

A further possibility is that the identifier is a reference that can be sent to a remote server to obtain some or all of the information specific to the replaceable component. Combinations of these implementations are also possible, in which the identifier includes some information specific to the replaceable component and also provides a reference to access other such information from the remote server.

The control system of the control device, which may be implemented for example by the control circuitry 175 shown in FIG. 1, compares the received identifier against the set of stored identifiers. In some cases this comparison may look for a direct match of the received identifier against a stored identifier. In other cases, a different form of comparison may be utilized. For example, the stored identifiers may be configured in pairs, each pair defining a range of model numbers. In this case, the comparison determines whether the received identifier falls within the range of model numbers defined by one or more pairs of model numbers (which can then be regarded as a match).

If the received identifier comprises multiple pieces of information, for example, multiple components, then two or more components could potentially be compared separately against the information of the stored identifiers (and more particularly, against the relevant components thereof). For example, a given identifier may comprise both a flavor of the material in the replaceable component and also operating parameters for use in heating this material.

The control device performs at least one control action for the electronic aerosol provision system dependent upon the result of comparing the received identifier against the stored identified. For example, if a match is found, the control device might perform one or more actions specific to the matched identifier, such as heating using a heating profile specific to the matched identifier, whereas if no match is found, the control device might utilize a default heating profile. In another example, if a match is found, the control device might allow operation of the electronic aerosol provision system to generate vapor, but if no match is found, the control device may provide a reduced level functionality for the electronic aerosol provision system. In one such case, if there is no match, operation is disabled (or not enable), such as because it cannot be confirmed that the replaceable component is compatible with the control device.

In some cases, the control action(s) may depend upon a binary outcome of the comparison (whether there is a match, yes or no), in other cases, some or all of the control(s) may depend on the particular match that is achieved. In the latter situation, different control actions may be associated with different stored identifiers (or groups or subsets of stored identifiers). These control actions may also be stored in memory 180, or may be stored elsewhere, but referenced from memory 180, thereby allowing the electronic aerosol provision system to perform one or more control action specific (and appropriate) to the particular matched identifier(s). In some cases multiple actions may be performed in response to a match (or matching of different components), for example, a heating profile may be selected, and information provided to the user on display 173. The action(s) performed may depend on which component(s) of an identifier find a matched in the stored identifiers.

The control device interacts with the remote server to update the set of stored identifiers. For example, the control device may use control information received from the remote server to add, delete, or modify one or more identifiers of the set of stored identifiers. In this way, the control device can be prepared, for example, for use with new types of replaceable component that may not have been available when the control device was originally sold. The control information may likewise be utilized to update the stored actions associated with the set of stored identifiers, for example, by modifying the control actions themselves, and/or by changing the association between different identifiers and different control actions.

In some cases, the remote server may push updated control information out to electronic aerosol provision devices, in other cases, the control system may send a request for updated control information from the remote server. For example, the control system may send such a request on a weekly basis, or perhaps whenever it establishes network connectivity (or some other set of criteria). The control system may also send a request for updated control information from the remote server in response to a received identifier not matching one of the stored identifiers. The control system may receive updated control information from the remote server in response to such a request, which can then be used to assess the received identifier as discussed above, i.e. by making a comparison of the received identifier against the updated set of stored identifiers, and then performing a control action for the electronic aerosol provision system dependent upon the result of this comparison.

In some cases, the electronic aerosol provision system is used with a replaceable component that forms a tobacco heated product (THP). In some cases, the aerosol precursor material in a consumable THP product may be more susceptible to variation, being directly derived from a natural product. Accordingly, the identifier in the consumable may be used to, for example, to indicate a particular blend of tobacco(s) or a particular batch of the consumable, and a heating profile that is chosen for such blend or batch.

While it has generally been described above that the container 120 is formed of a plastics material and includes a portion of solid aerosol precursor material therein, in other implementations the container 120 may be formed of a paper or card material. In some implementations, the paper or card material is wrapped around the outer surface of aerosol forming material formed substantially into a rod-shape. Such a container 120 may be formed in a similar manner to combustible cigarettes, and may also include an integrated mouthpiece (e.g., a filter) at one end thereof. The general approach of heating the container described above still applies, namely the container is heated, but not burnt, to generate an inhalable aerosol. With these containers, the identifiers may be provided in any suitable manner as described above, e.g., they may be optically printed on the surface of the container.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc., other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. A control device for an electronic aerosol provision system, the control device being configured to receive a replaceable component to form an electronic aerosol provision system, the control device including:
   a communication interface for performing communications external to the electronic aerosol provision system;
   a memory configured to hold a set of stored identifiers; and
   a control system configured to:
      receive control information from a remote server via the communication interface;
      update the set of stored identifiers based on the control information received from the remote server;
      receive an identifier from a replaceable component received by the control device;
      make a comparison of the received identifier against the set of stored identifiers; and
      perform a control action for the electronic aerosol provision system dependent upon the result of the comparison.

2. The control device of claim 1, wherein updating the set of stored identifiers based on the control information comprises at least one of:
   adding one or more identifiers to the set of stored identifiers;
   removing one or more identifiers from the set of stored identifiers; and
   modifying one or more identifiers in the set of stored identifiers.

3. The control device of claim 1, wherein if the received identifier does not match one of the set of stored identifiers, the control device is configured to provide reduced functionality for the electronic aerosol provision system compared with functionality available for the electronic aerosol provision system if the received identifier matches one of the set of stored identifiers.

4. The control device of claim 3, wherein the reduced functionality includes the control device not enabling operation of the electronic aerosol provision system for generating an aerosol.

5. The control device of claim 1, wherein if the received identifier does not match one of the set of stored identifiers, the control action comprises a default action.

6. The control device of claim 5, wherein the default operation comprises preventing operation of the electronic aerosol provision system for aerosol production.

7. The control device of claim 5, wherein the default operation comprises allowing operation of the electronic aerosol provision system for aerosol production according to one or more default settings.

8. The control device of claim 1, wherein if the received identifier matches one of the set of stored identifiers, the control action comprises a stored action associated with the stored identifier that matches the received identifier.

9. The control device of claim 8, wherein the control system is further configured to update the stored actions associated with the set of stored identifiers based on the control information received from the remote server.

10. The control device of claim 8, wherein the memory is configured to hold the stored actions associated with the set of stored identifiers.

11. The control device of claim 1, wherein the control system is further configured to periodically request updated control information from the remote server.

12. The control device of claim 1, wherein the control system is further configured to send a request for updated control information from the remote server in response to the received identifier not matching one of the set of stored identifiers.

13. The control device of claim 12, wherein the request for updated control information includes the received identifier.

14. The control device of claim 13, wherein the control system is further configured to:
update the set of stored identifiers based on updated control information received from the remote server in response to the request;
make a comparison of the received identifier against the updated set of stored identifiers; and
perform an updated control action for the electronic aerosol provision system dependent upon the result of the comparison.

15. The control device of claim 1, wherein each identifier represents a different type or class of replaceable component.

16. The control device of claim 1, wherein the replaceable component comprises an aerosol precursor material.

17. The control device of claim 16, configured to aerosolize the aerosol precursor material located in the replaceable component.

18. An electronic aerosol provision system including the control device of claim 1.

19. The electronic aerosol provision system of claim 18, wherein the replaceable component comprises a tobacco heated product.

20. A method of operating a control device for an electronic aerosol provision system, the control device being configured to receive a replaceable component to form the electronic aerosol provision system, the method comprising:
storing a set of identifiers in the control device;
receiving control information from a remote server via a communication interface of the control device;
updating the set of stored identifiers based on the control information received from the remote server;
receiving an identifier from a replaceable component received by the control device;
comparing the received identifier against the set of stored identifiers; and
performing a control action for the electronic aerosol provision system dependent on the result of the comparing.

* * * * *